United States Patent [19]

Mathias et al.

[11] Patent Number: 5,330,464
[45] Date of Patent: Jul. 19, 1994

[54] RELIABLE BREAKABLE CLOSURE MECHANISM

[75] Inventors: Jean-Marie Mathias, Lillois; Jean-Claude Bernes, Faimes; Ermenegildo Lavezzo, Souvret; Jack Debrauwere, Halle, all of Belgium

[73] Assignee: Baxter International Inc., Deerfield, Ill.

[21] Appl. No.: 849,267

[22] Filed: Mar. 11, 1992

[51] Int. Cl.$^5$ .............................................. A61M 5/00
[52] U.S. Cl. ................................ 604/415; 604/408; 604/403
[58] Field of Search ............. 604/403, 408, 410, 415, 604/416

[56] References Cited

U.S. PATENT DOCUMENTS

| | | | |
|---|---|---|---|
| 3,217,710 | 11/1965 | Beall et al. | 604/408 |
| 3,750,645 | 8/1973 | Bennett et al. | 604/403 X |
| 4,007,738 | 2/1977 | Yoshino | |
| 4,181,140 | 1/1980 | Bayham et al. | |
| 4,294,247 | 10/1981 | Carter et al. | |
| 4,340,049 | 7/1982 | Munsch | 604/408 X |
| 4,430,049 | 2/1984 | Aiba | |
| 4,479,989 | 10/1984 | Mahal | 604/408 X |
| 5,188,629 | 2/1993 | Shimoda | 604/403 X |

FOREIGN PATENT DOCUMENTS

| | | | |
|---|---|---|---|
| 330130 | 8/1989 | European Pat. Off. | 604/408 |
| 3238836 | 8/1988 | Fed. Rep. of Germany. | |
| 572176 | 9/2945 | United Kingdom | 604/403 |
| 9111152 | 8/1991 | World Int. Prop. O. | 604/403 |

Primary Examiner—Robert A. Hafer
Assistant Examiner—Sam Rimell
Attorney, Agent, or Firm—Bradford R. L. Price; Paul C. Flattery; Robert M. Barrett

[57] ABSTRACT

A frangible seal for a fluid path including a frangible seal member secured within a tube defining the fluid path. The frangible seal member having a tubular seal member and a stem extending from the tubular seal member which, upon bending back and forth, breaks away from the seal member thereby to rupture the tubular seal in the fluid path. The tubular seal member and stem are integrally formed of a non-PVC material. The tubular seal member will bond to PVC tubing during steam heating thereof. The tubular seal member and stem are constructed to provide uniform non-reclosable rupturing. The stem includes vanes with spurs that frictionally engage the inner walls of the tube to maintain separation of the stem and ruptured tubular seal member.

12 Claims, 4 Drawing Sheets

RELIABLE BREAKABLE CLOSURE MECHANISM

BACKGROUND OF THE INVENTION

The present invention generally relates to frangible seals, i.e. breakable closures, for allowing fluid communication in a sealed conduit. More particularly, the invention relates to a frangible seal for providing fluid communication between a plurality of isolated containers, for example blood bags.

In a variety of applications, it is desirable to separately store components of a mixture for subsequent mixing. The components can be separated and isolated by what hereinafter generically will be referred to as a frangible seal, which is ruptured to provide communication between containers in which the separate components are stored.

Additionally, in the area of blood transfusions, whole blood is rarely used to perform a transfusion. Instead, in order to make an effective use of the blood, it is separated into components and the various components are placed in separate bags.

To this end, there has been provided a so-called multiple bag which is integral, closed and sterile-sealed, and may be manipulated wholly from outside itself and in which a plurality of plastic blood bags are mutually connected by means of connection tubes. Whole blood is collected into a collecting bag and thus, subject to centrifugation thereby to separate the components. However, to prevent unseparated blood from scattering into a connection tube, a rupturable seal is provided.

In another related field, a procedure known as continuous ambulatory peritoneal dialysis is used to treat End Stage Renal Disease. The continuous ambulatory peritoneal dialysis procedure is intended to be a patient self-care technique once a catheter is surgically implanted in the patient. In this procedure, a dialysis solution is infused into the peritoneal cavity of the patient. The dialysis solution is stored in a bag that can be connected to the catheter.

In both of these fields, frangible seals and flexible tubes are used to effect communication between the blood bags or the dialysis solution and the catheter, respectively.

In this regard, in U.S. Pat. No. 4,007,738, there is discussed a mechanism for allowing blood bags to communicate with each other comprising a connection pipe; a connection tube for connecting a first blood bag to a second blood bag, the connection tube being fitted into and secured to the connection pipe having a sealed portion, one end thereof on the side of the second blood bag being fitted into and secured to the connection tube; and a breakable small thickness section formed at the communication pipe between the sealed portion and the secured end thereof. Communication between the first and second bags is rendered effective by breaking the communication pipe at the small thickness portion.

In U.S. Pat. No. 4,181,140, there is disclosed a frangible resealable closure for a flexible tube having hold open means. Valve means in a flexible tube, for example, tubing for connecting blood bags, are provided which comprises a tubular portion having a closed end, and an elongated generally rigid member carried on the exterior of the closed end and positioned within the flexible tube. Frangible means are provided to permit the opening of the closed end by manual manipulation of the elongated member from outside of the flexible tube.

The elongated, rigid member is adapted to fit in sealing relationship within the tubular portion after opening of the closed end, to permit resealing of the valve. The elongated, generally rigid member carries longitudinal vanes to provide flow channels along its length. A pair of the vanes in opposed relationship extend rearwardly of the end of the central portion of the rigid member, and the flexible tube defines a bore portion positioned to receive and resiliently hold the opposed vanes when the frangible means is broken and the rigid member is separated from the tubular portion.

It is discussed that the vanes may be of unequal length. The flexible tube surrounding the rigid member may then define a conical portion, positioned to receive and resiliently hold the longer vanes after the frangible means have been broken and the rigid member separated from the tubular portion.

The elongated, generally rigid member also includes a tapered portion for fitting within the bore of the tubular portion after opening for reclosing the structure again. Thus, the discussed frangible seal also functions as a frangible resealable closure.

However, studs are provided to project outwardly from the elongated, rigid member to prevent the accidental complete insertion of the elongated member into the bore which could render the removal of the member difficult at a later time. The studs bear against the end of the tubular portion when the elongated member is inserted into its proper depth, preventing further insertion.

In U.S. Pat. No. 4,294,247 there is discussed another frangible, resealable closure for a flexible tube.

In U.S. Pat. No. 4,340,049 there is discussed another frangible seal in the form of a break-away valve comprising two parts: a tubular portion with a closed end; and an elongated, generally rigid handle breakably attached to the closed end. The elongated handle has projections which frictionally contact the interior surface of the flexible tube and prevent the elongated handle from moving back into a closed position once the elongated handle has been broken.

The valve may be used in conjunction with tubing and a plastic container of a dialysis solution. The valve is opened by breaking away the elongated, generally rigid handle and moving (i.e., "walking") the rigid handle down the tube by folding the tube back and forth upon itself. The projections of the rigid break-away handle have sufficient frictional contact with the inside of the tube to assure that the handle will not move back into contact with the tubular portion, and the valve will remain open.

SUMMARY OF THE INVENTION

The present invention provides an improved frangible seal for a fluid path. To this end, the invention provides a frangible seal for a fluid path with more uniform rupturing. Moreover, the invention provides a fluid path frangible seal with greater flow area after rupturing of the seal.

In an embodiment, the invention provides a frangible seal member comprising a rigid plastic tubular seal member with an attached rigid plastic elongated member or stem. The seal member includes a closed end from the exterior of which the stem axially extends. The seal member and stem are formed of a non-polyvinyl chloride material.

In an embodiment, the invention provides that the non-polyvinyl chloride material is a polycarbonate.

In an embodiment, the invention provides that the stem includes vanes with spurs projecting outwardly from the stem. At the base of the stem are included several "flying buttresses" projecting outwardly from the stem. These flying buttresses are constructed so that they engage a bottom interior rib in a tubing in which the frangible seal member is positioned. These flying buttresses are designed so that they frictionally contact the interior surface of the flexible tube. When the tube is externally folded back and forth upon itself, the stem moves only one way and the leading edge corners of the flying buttresses as well as the bottom interior rib prevent the stem from moving back into a closed position once the stem has been broken.

In an embodiment, at the top of the stem are included spurs projecting outwardly from the stem. These spurs do not interfere with the interior surface of the tube before rupture, but as soon as the tube is folded the spurs frictionally engage inside a compartment or chamber of the tube having a slightly smaller inside diameter. This chamber also comprises a second interior rib. A folding of the tube back and forth breaks the stem with a click noise and the stem moves upwardly in the tube, progressively separating from the tubular portion.

In an embodiment, the invention provides a frangible seal comprising a tubular housing through which fluid communication is to be made and a frangible seal member positioned therein. The tubular housing comprises one chamber with a first diameter and a first interior rib in which the unruptured frangible seal member is positioned and an adjacent chamber with a second interior rib. The frangible seal member is as described above and the tubular seal member is secured in sealing engagement to the interior of the first chamber.

In an embodiment, the invention provides a tubular housing wherein the second chamber has a reduced diameter with respect to the first chamber.

In yet another embodiment, the invention provides a delivery system comprising two containers interconnected for fluid communication by a flexible tubing, the tubing being coupled to a tubular housing which, in turn, is coupled to one of the containers. The tubular housing preferably is as described above. Disposed within the tubular housing is a frangible seal member as described above.

In a preferred embodiment, the tubular seal member of the frangible seal member is press-fitted inside the tubular housing at a sufficient depth to allow for radio-frequency sealing of the tubular housing to the sheetings of a bag, but with the tubular frangible seal member being placed outside of the radio-frequency seal area so that it will seal to the inner walls of the tubular housing by fusing thereto during heat sterilization. Such fusing or adhesive properties are described, for example in German Patent No. De 32 38 836, the teachings of which are fully incorporated herein by reference.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

In accordance with the invention, a frangible seal can be provided for a fluid path wherein a frangible seal member is secured in sealing engagement within a fluid path conduit, the conduit including two retaining ribs. The frangible seal member can include a tubular seal member with a closed end and a stem integrally attached to the exterior of the closed end and extending axially therefrom.

The seal member and stem can be integrally formed of a non-PVC material so that the frangible seal member will adhere to the fluid path conduit during heating, for example during heat sterilization, thereof. Further, the stem can be provided with vanes having spurs and flying buttresses that are so constructed and arranged that upon separation of the stem from the seal member, a bottom rib in the interior of the conduit will engage the flying buttresses to maintain the stem and seal member in separated positions while a top rib in the interior of the conduit prevents the spurs rom occluding the end portion of the conduit.

Figure 1:
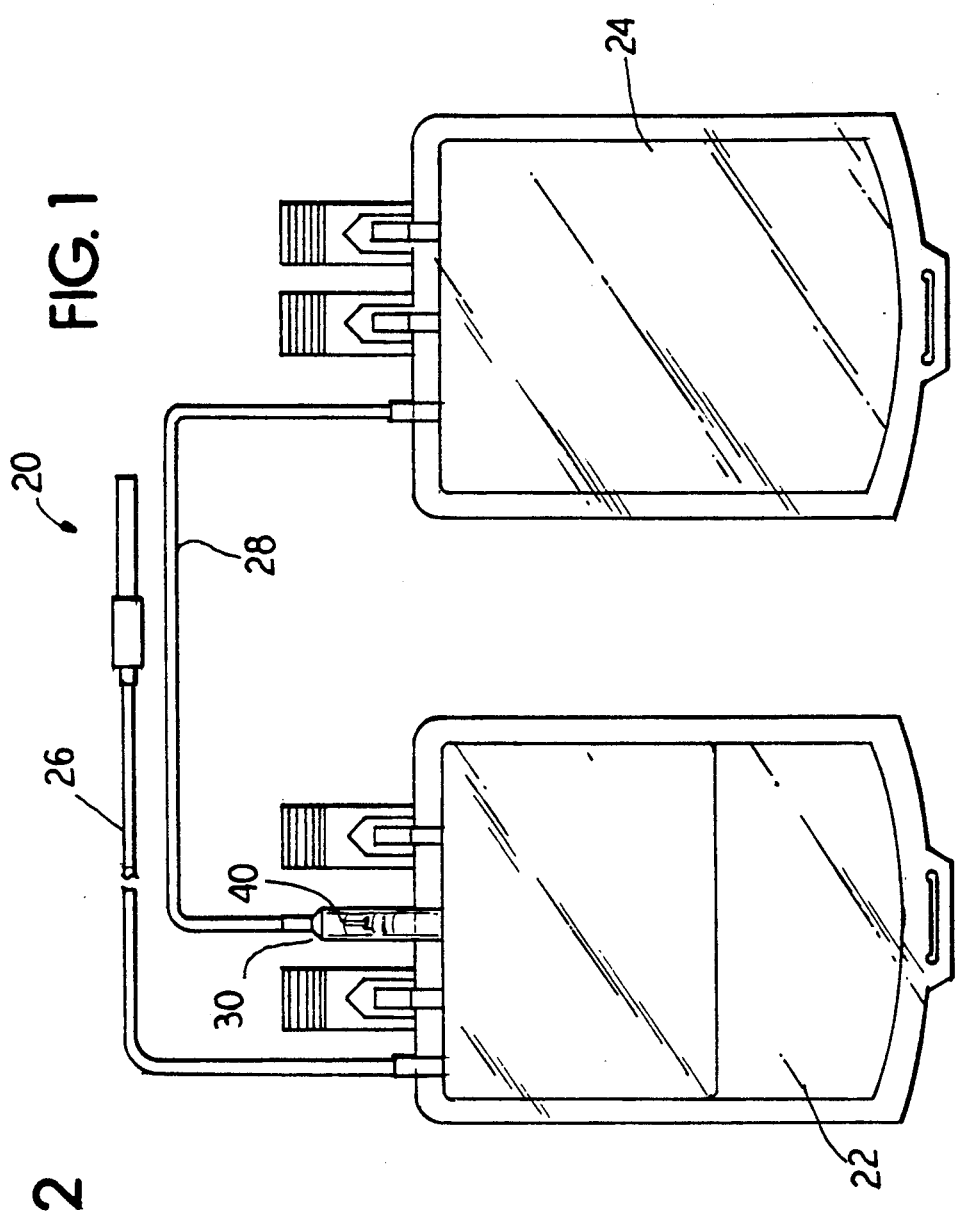
FIG. 1 illustrates a double blood bag system for which the present invention is particularly useful.

In FIG. 1 there is illustrated a double blood bag system 20 for which the present invention is particularly useful. Of course, the illustrated system 20 is merely illustrative of the many uses to which the present invention can be put.

In the double blood bag system 20 of FIG. 1, a first bag 22 initially contains an anticoagulant solution which is isolated from an empty bag 24 with a conduit 28 comprising flexible polyvinyl chloride (PVC) tubing. After collection through the donor tube 26 of whole blood in the bag 22, the double blood bag system is spun to separate, or sediment, out the blood cells from the plasma. The plasma is then expressed with an extractor from the collection bag 22 into the second bag 24 after rupturing of the frangible seal 40.

A flexible conduit or tube 28, made of, for example PVC, is secured for fluid communication between bags 22 and 24. In a tubular housing 30 via which the tubing 28 is secured to the bag 22, a frangible seal member 40 is positioned, thereby to provide the frangible seal between the two bags 22 and 24.

Initially, the frangible seal 40 prevents fluid communication between the bags 22 and 24. However, upon proper rupturing of the seal 40, fluid communication is permitted between the bags 22 and 24. With blood bag systems, it is particularly important to ensure reliable maintenance of the flow once the frangible seal has been ruptured. Moreover, it is important to minimize the blood flow restriction in the seal.

Figure 2:
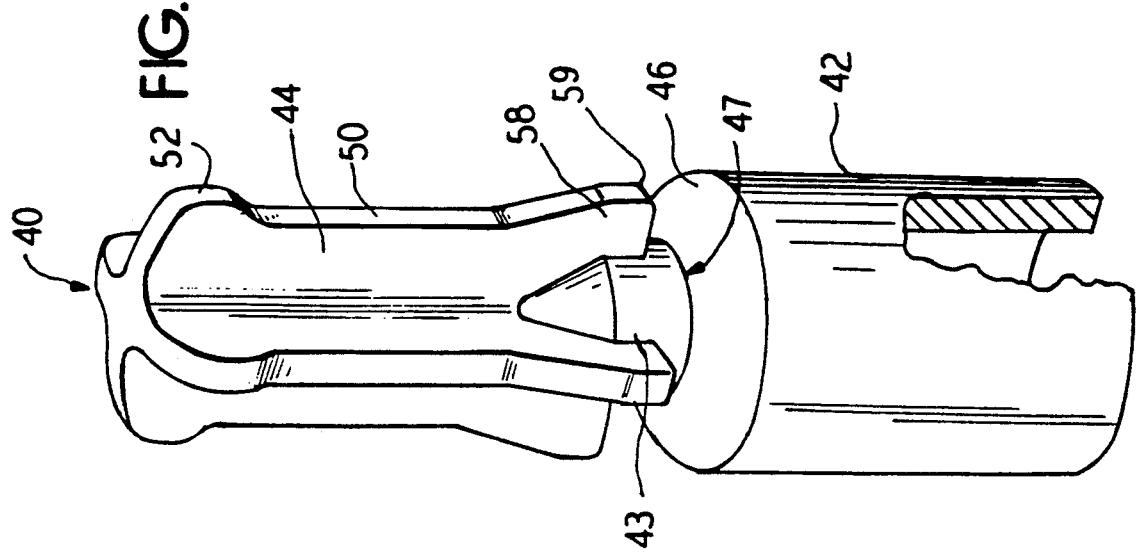
FIG. 2 illustrates in perspective view an unruptured frangible seal member of the present invention.
Figure 4:
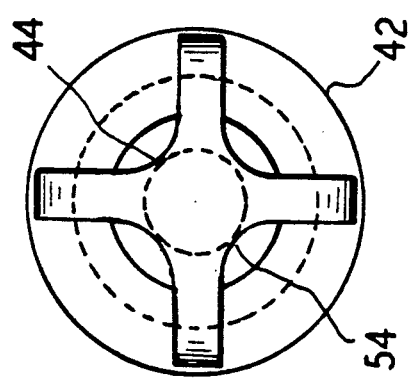
FIG. 4 illustrates an end view of the frangible seal member of FIGS. 2 and 7.
Figure 3:
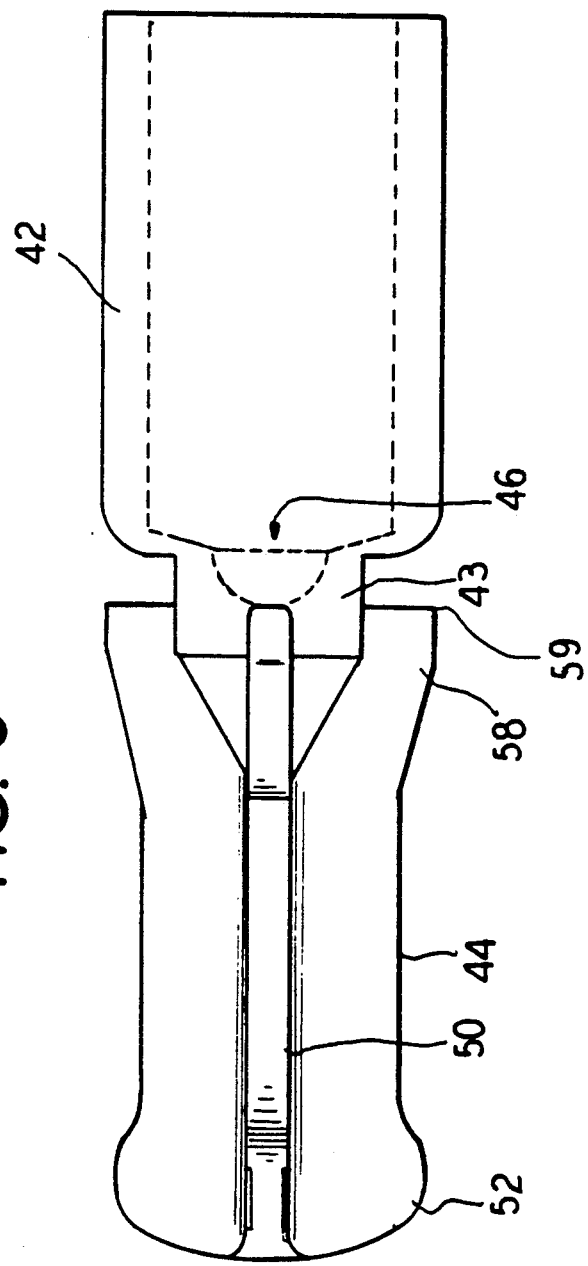
FIG. 3 illustrates a side view of the frangible seal member of FIG. 2.

To this end, a frangible seal member 40 such as that illustrated in FIGS. 2–4 is provided by the present invention. With reference to FIGS. 2–4, the frangible seal member 40 will now be described in greater detail.

As illustrated, the frangible seal member 40 includes a tubular seal member 42 and an elongated, rigid member or stem 44 extending therefrom. The tubular seal member 42 generally comprises a tubular portion having a closed end 46 from the exterior of which axially extends the stem 44.

By bending the stem 44 back and forth one is able to rupture the stem 44 along a path 47 at the base of the cylindrical portion 43. This allows the stem 44 to be separated from the closed end 46 of the seal member 42 thereby permitting flow therethrough.

The rupture of the closed end 46 is made easier and more reliable by the choice of a rigid non-polyvinyl chloride plastic material, for example, polycarbonate. Polycarbonate is a preferred material because its hardness and dimensions remain unchanged during heat sterilization.

The closed end 46 of the tubular seal member 42 preferably comprises a seal membrane 47 whose thickness, in sectional view, diminishes from the outside to the inside of the tubular portion. The membrane us designed so that the rupture takes place along the thinnest area which corresponds tot eh path having the diameter of the cylindrical portion 43. With this construction, the rupture is forced to become localized along a given circle where the membrane thickness is minimal 47.

The choice of a polycarbonate as the plastic material, also provides a frangible seal member 40 with strong mechanical resistance to movement of the stem 44 and allows for reduced sizing of the stem 44. As illustrated in FIGS. 6–9, the reduced diameter of a central axial portion 54 of the stem 44 provides an appreciably clear annular passage for fluid between the stem 44 and an inner diameter of the tubular housing 30. In the illustrated blood bags application, the section surface of this passage is more than twice that of the sectional surface of prior arrangements.

As also illustrated in FIGS. 2–4, the stem 44 preferably includes four vanes 50 extending radially therefrom at the outer extremities of which are formed four respective spurs 52. These spurs 52 serve to frictionally engage with inner walls 45 of the second chamber 62 of the conduit once the frangible seal is broken by back and forth bending of the stem 44.

During the back and forth bending of the tube, the flying buttresses 58 engage the first interior vane 50 while the spurs 52 engage the restricted second chamber 62. The successive back and forth bending moves the stem 44 away from the tubular portion 42 by "walking" or "creeping" up the cannula housing 30. The top interior rib 53 limits the progression of the stem so that the end portion of the housing 64 mating to the tubing is not occluded by the spurs 52. The top and bottom interior ribs maintain the stem 44 and tubular seal member 42 in spaced apart relation.

The progression of the stem 44 towards the top interior rib 53 by successive bending is made easier by the presence of the four flying buttresses 58 that also extend radially from the stem 44. These flying buttresses 58 are designed with leading edge corners 59 that are oriented so that they facilitate the axial insertion of the frangible seal member 40 in the cannula housing 30 as well as the creeping up effect during the bending.

The foregoing construction is particularly applicable in situations where during compression of the bags 22 and 24, the frangible seal undergoes favorable and non-favorable flow directions. The stem 44 is held separated from the seal member 42 no matter what direction the fluid flows.

Figure 5:
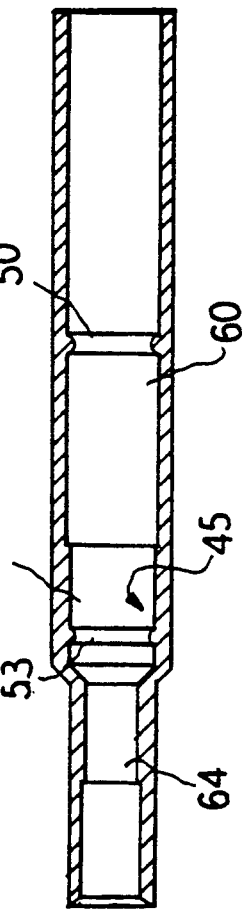
FIG. 5 illustrates in longitudinal sectional view a cannula housing for use with the frangible seal member of FIGS. 2-4.
Figure 3A:
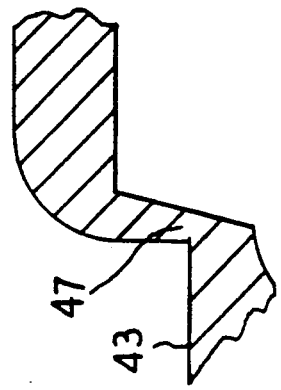
FIG. 3A illustrates a detail of the frangible seal of FIG. 3.

In FIG. 5, there is illustrated in greater detail the tubular housing 30 of FIG. 1. As illustrated, the tubular housing 30 is generally tubular and includes three interconnected and axially aligned chambers 60, 62, and 64. The first chamber 60 is constructed to fit into an opening in the edge of the seal of the bag 22, i.e. between the sheetings thereof, and to be sealed therein by means of, e.g., radio frequency welding. It includes an interior rib 56. This rib 56 is constructed for engagement with the leading edge corners 59 of the stem 44 once the stem has been separated from the tubular seal member 42, as previously described.

The second chamber 62 preferably has a relatively smaller interior diameter with respect to that of the first chamber 60 and includes another interior rib 53. This rib 53 is constructed for limiting the progression of the stem 44, as previously described.

The third chamber 64 has a relatively smaller interior diameter than that of the second chamber 62 as well as a reduced outer diameter so as to mate with the flexible tubing 28. The reduced interior diameter is protected from being occluded by the spurs 52 of the stem 44 by the second interior rib 53.

The first and second chambers 60 and 62 are constructed to have lengths such that the leading edge corners 59 of the stem 44 will not engage the bottom interior rib 56, unless and until the stem 44 has been separated from the seal member 42. Moreover, the lengths are selected so that once the flying buttresses 58 do so engage the rib 56, the stem 44 is maintained at a distance from the seal member 42 to ensure adequate flow through the rupture opening in the seal member 42.

Figures 6, 7:
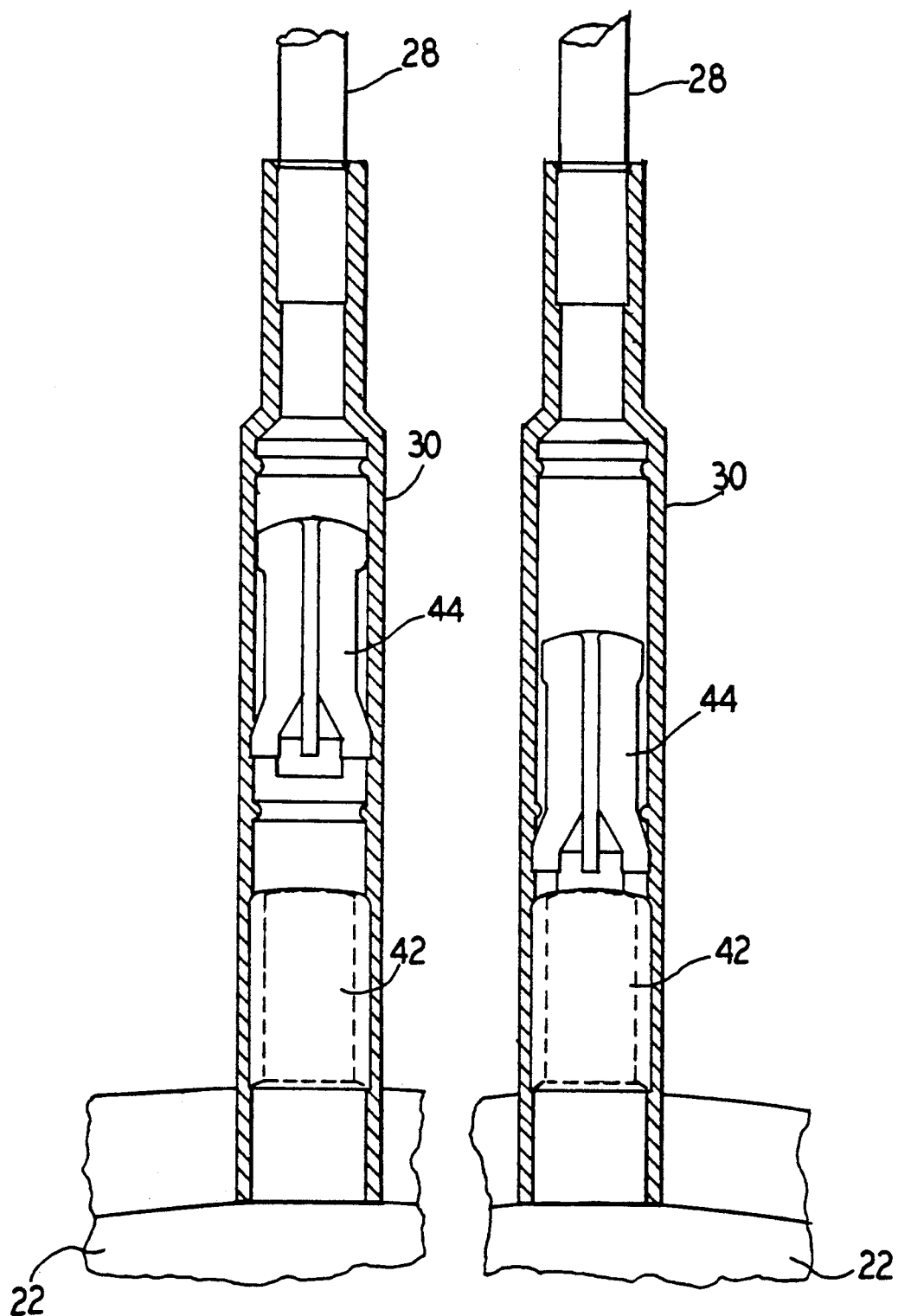
FIG. 6 illustrates in longitudinal sectional view a cannula with an unruptured frangible seal member.
FIG. 7 illustrates in longitudinal sectional view a cannula with a ruptured frangible seal member.

In FIGS. 6 and 7, the rupture of the frangible seal member 40 is illustrated. As illustrated in FIG. 6, initially the frangible seal member 40 is secured within a suitable tubular housing, such as the illustrated tubular housing 30, such that the tubular seal member 42 is sealingly secured to the interior of the walls of the chamber 60. This sealing engagement is provided by the fusion or adhesion of the non-PVC seal member 42 to the PVC tubular housing 30 during heat sterilization. The spurs 52 of the stem 44 do not adhere to the tubular housing because the interior diameter of the chamber 60 is sufficiently larger than the overall diameter of the spurs 52.

As illustrated in FIG. 7, once the frangible seal 40 is ruptured by back and forth bending of the stem 44, the stem 44 is caused to "walk" or "creep" away from the seal member 42 until the spurs 52 are captured within the second chamber 62. At that time, four channels are provided by the vanes 50 through which fluid such as blood components can flow. As discussed above, the use of a non-PVC material in the formation of the stem 44 allows for a reduced diameter central portion 54 thereby allowing for enlarged flow channels through the vanes 50.

Figures 8, 9:
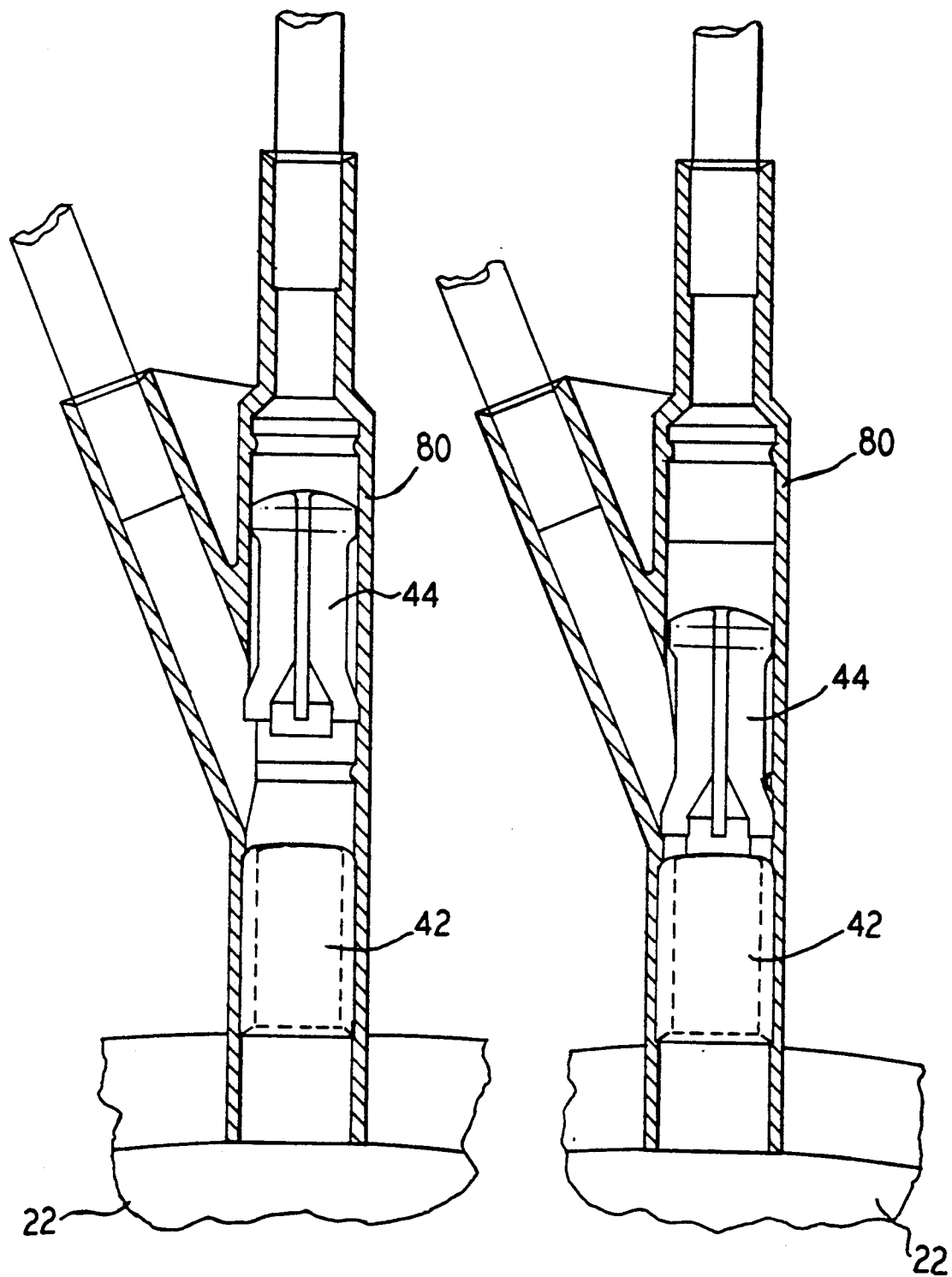
FIG. 8 illustrates in longitudinal sectional view a Y-shaped cannula with an unruptured frangible seal member.
FIG. 9 illustrates in longitudinal sectional view a Y-shaped cannula with a ruptured frangible seal member.

As illustrated in FIGS. 8 and 9, a frangible seal member such as the frangible seal member 40 can also be used in a Y-shaped tubular housing 80, by making necessary modifications.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A fluid path having a frangible seal, comprising:
   a substantially tubular housing having first, second, and third chambers aligned along an axis, the first chamber including an interior rib, the second chamber interconnecting the first and third chambers, the second chamber having an interior rib; and
   a frangible seal member secured within the first chamber of the tubular housing, the frangible seal member made of a rigid, non-polyvinylchloride plastic and comprising:
   a tubular seal member secured in sealing engagement to the interior of the first chamber, the tubular seal member having a closed end with a rupturable membrane facing the second chamber of the tubular housing;
   a stem attached to and extending axially from the rupturable membrane of the tubular seal member toward the second chamber of the tubular housing; and
   a plurality of vanes extending radially from the stem, at least two of the vanes having spurs formed on extremities thereof and constructed to frictionally engage the inner walls of the second chamber of the tubular housing when the stem is separated from the tubular seal member.

2. The fluid path of claim 1, wherein the rupturable membrane of the closed end of the tubular seal member includes an annular edge disposed interiorly of an outer periphery of the tubular seal member to provide a path along which rupturing of the membrane can be initiated.

3. The fluid path of claim 1, wherein the non-polyvinylchloride plastic employed in the frangible seal member is a polycarbonate.

4. The fluid path of claim 1, wherein the frangible seal member includes a plurality of flying buttresses located on a second extremity of the vanes.

5. A delivery system, comprising:
   two containers;
   a flexible tubing interconnecting the two containers for fluid communication therebetween;
   a substantially tubular housing secured in fluid communication to one container, the tubular housing having first, second, and third chambers aligned along an axis, the second chamber interconnecting the first and third chambers, the first and the second chambers having an interior rib; and
   a frangible seal member secured within the tubular housing, the frangible seal member made of a rigid, non-polyvinylchloride plastic and comprising:
   a tubular seal member secured in sealing engagement to the interior of the first chamber, the tubular seal member having a closed end with a rupturable membrane facing the second chamber of the tubular housing;
   a stem attached to and extending axially from the rupturable membrane of the tubular seal member to the second chamber of the tubular housing; and
   a plurality of vanes extending radially from the stem, at least two of the vanes having spurs formed on extremities thereof and constructed to frictionally only engage the inner walls of the second chamber of the tubular housing when the stem is separated from the tubular seal member.

6. The delivery system of claim 5, wherein the non-polyvinyl chloride plastic used to form the frangible seal member is a polycarbonate.

7. The delivery system of claim 5, wherein the closed end of the tubular seal member is of diminishing thickness proceeding from an outside edge to an internal axis of the frangible seal member.

8. The delivery system of claim 5, wherein the frangible seal member includes a plurality of flying buttresses located at a second extremity of the vanes.

9. The delivery system of claim 8, wherein the flying buttresses are designed to frictionally engage the interior ribs of the first chamber.

10. The delivery system of claim 8, wherein the flying buttresses include leading edges to facilitate the axial insertion of the frangible seal in the tubular body.

11. A frangible seal member, comprising
    a rigid non-polyvinyl chloride plastic tubular seal member having a closed end with a frangible portion wherein the closed end of the tubular seal member is of diminishing thickness proceeding toward an internal axis of the frangible seal member from an outside edge;
    a rigid non-polyvinyl chloride plastic stem integrally formed with the tubular seal member and extending axially from an exterior of the frangible portion and so constructed and arranged that back and forth bending of the stem will cause the frangible portion to rupture thereby forming an opening in the closed end of the tubular member;
    at lest two vanes formed on the stem and extending therefrom at right angles, each of the at least two vanes terminating in a spur; and
    a plurality of extended members formed on the stem at another end of the vanes and extending at right angles from the stem.

12. A flow path having a frangible seal, comprising:
    a tubular housing; and
    a frangible seal member secured in the tubular housing, the frangible seal member comprising:
    a rigid non-polyvinyl chloride plastic tubular seal member having a closed end with a frangible portion wherein the closed end of the tubular seal member is of diminishing thickness proceeding from an outside edge toward an internal axis of the frangible seal member;
    a rigid non-polyvinyl chloride plastic stem integrally formed with the tubular seal member and extending axially from an exterior of the frangible portion such that back and forth bending of the stem will cause the frangible portion to rupture thereby forming an opening in the closed end of the tubular member;
    a plurality of vanes formed on the stem and extending therefrom at right angles, at least two of the plurality of vanes terminating in a spur; and
    a plurality of flying buttresses formed on the stem at another end of the vanes and extending at right angles from the stem.

* * * * *